United States Patent [19]
Isbister

[11] Patent Number: 5,935,799
[45] Date of Patent: Aug. 10, 1999

[54] BIOLOGICAL ASSAY FOR MICROBIAL CONTAMINATION

[75] Inventor: Jenefir D. Isbister, Potomac, Md.

[73] Assignee: George Mason University, Fairfax, Va.

[21] Appl. No.: 08/988,239

[22] Filed: Dec. 10, 1997

[51] Int. Cl.[6] .................. G01N 33/569; G01N 21/29; C12Q 1/34; C12Q 1/06

[52] U.S. Cl. .................. 435/7.37; 422/82.05; 422/82.08; 435/4; 435/4.5; 435/7.35; 435/18; 435/34; 435/38; 435/39

[58] Field of Search .................. 422/82.05, 82.08; 435/4, 4.5, 7.35, 18, 34, 38, 39, 7.37

[56] References Cited

U.S. PATENT DOCUMENTS

| | | | |
|---|---|---|---|
| 5,159,799 | 11/1992 | Rising et al. | 53/433 |
| 5,393,662 | 2/1995 | Roth et al. | 435/38 |
| 5,411,867 | 5/1995 | Chang et al. | 435/18 |
| 5,510,243 | 4/1996 | Boyd et al. | 435/18 |
| 5,527,667 | 6/1996 | Ijzerman et al. | 435/5 |
| 5,643,743 | 7/1997 | Chang et al. | 435/34 |

OTHER PUBLICATIONS

Baxter Diagnostics Inc., "Scientific Products Catalogue, 1991–1992", p. 379, Jan. 1, 1991.
Frampton et al, "Methods for *Escherichia coli* identification in food, water and clinical samples based on beta–glucuronidase detection", J. Applied Bacteriol., vol. 74, pp. 223–233, Jan. 1, 1993.
Liksdal et al, "Monitoring of fecal pollution in coastal waters by use of rapid enzymatic techniques", Appl. Environ. Microbiol., vol. 60, No. 5, pp. 1581–1584, May 1, 1994.
Venkateswaran et al, "Comparison of commercially available kits with standard methods for the detection of coliforms and *Escherichia coli* in foods", Appl. Environ. Microbiol., vol. 62, No. 7, pp. 2236–2243, Jul. 1, 1996.

*Primary Examiner*—James C. Housel
*Assistant Examiner*—Rodney P. Swartz
*Attorney, Agent, or Firm*—Birch, Stewart Kolasch & Birch, LLP

[57] ABSTRACT

A semi-quantitative method for determining the concentration of viable coliforms or *E. coli* in a liquid is provided. The sample to be tested is mixed with an indicator reagent which includes a specific indicator compound that undergoes a change that is detectable by spectrophotometric or visual methods upon cleavage by a beta galactosidase enzyme found in coliforms or a beta glucuronidase enzyme unique to *E. coli*.

25 Claims, 3 Drawing Sheets

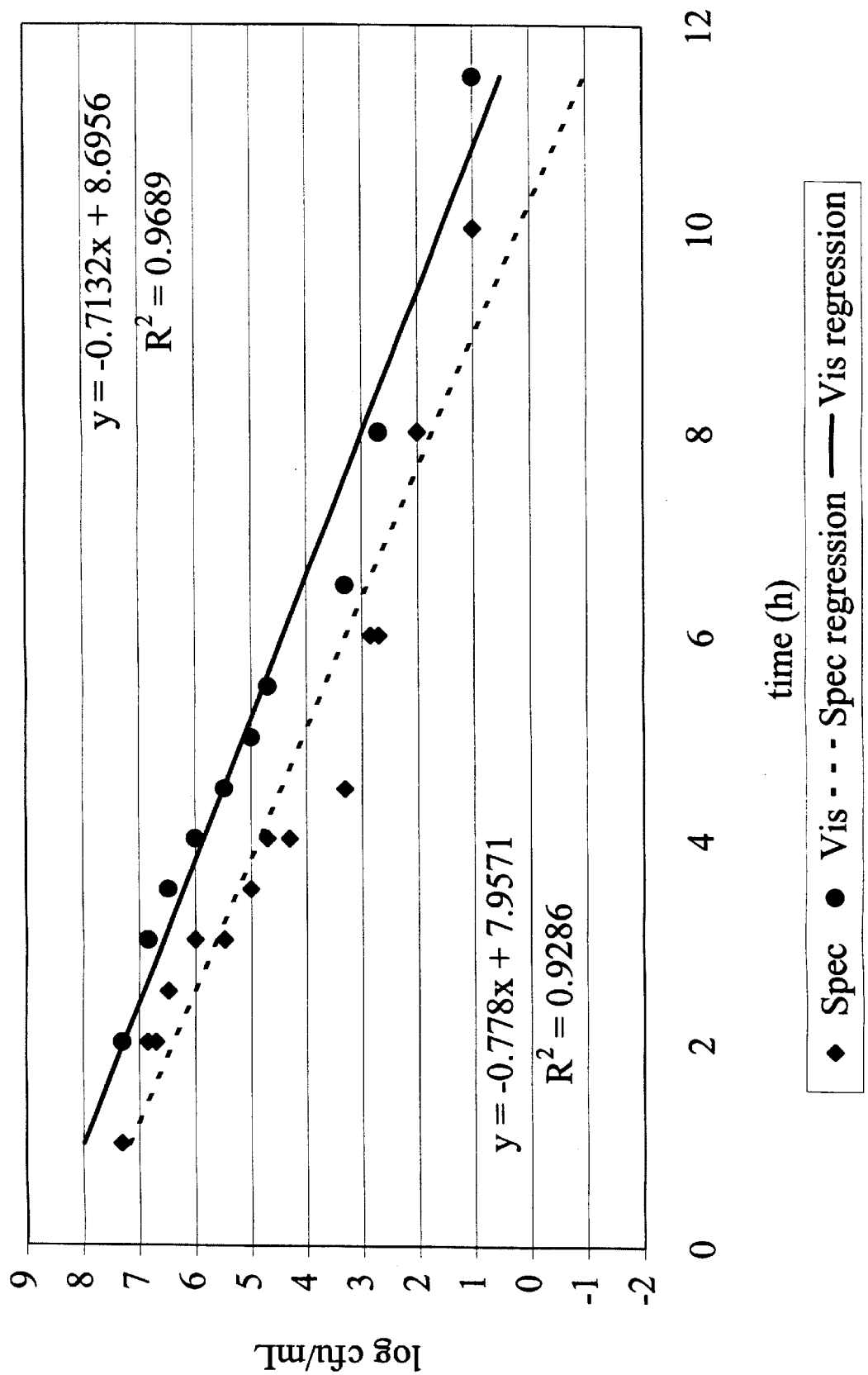
FIG 4: Coliform Correlation Curves

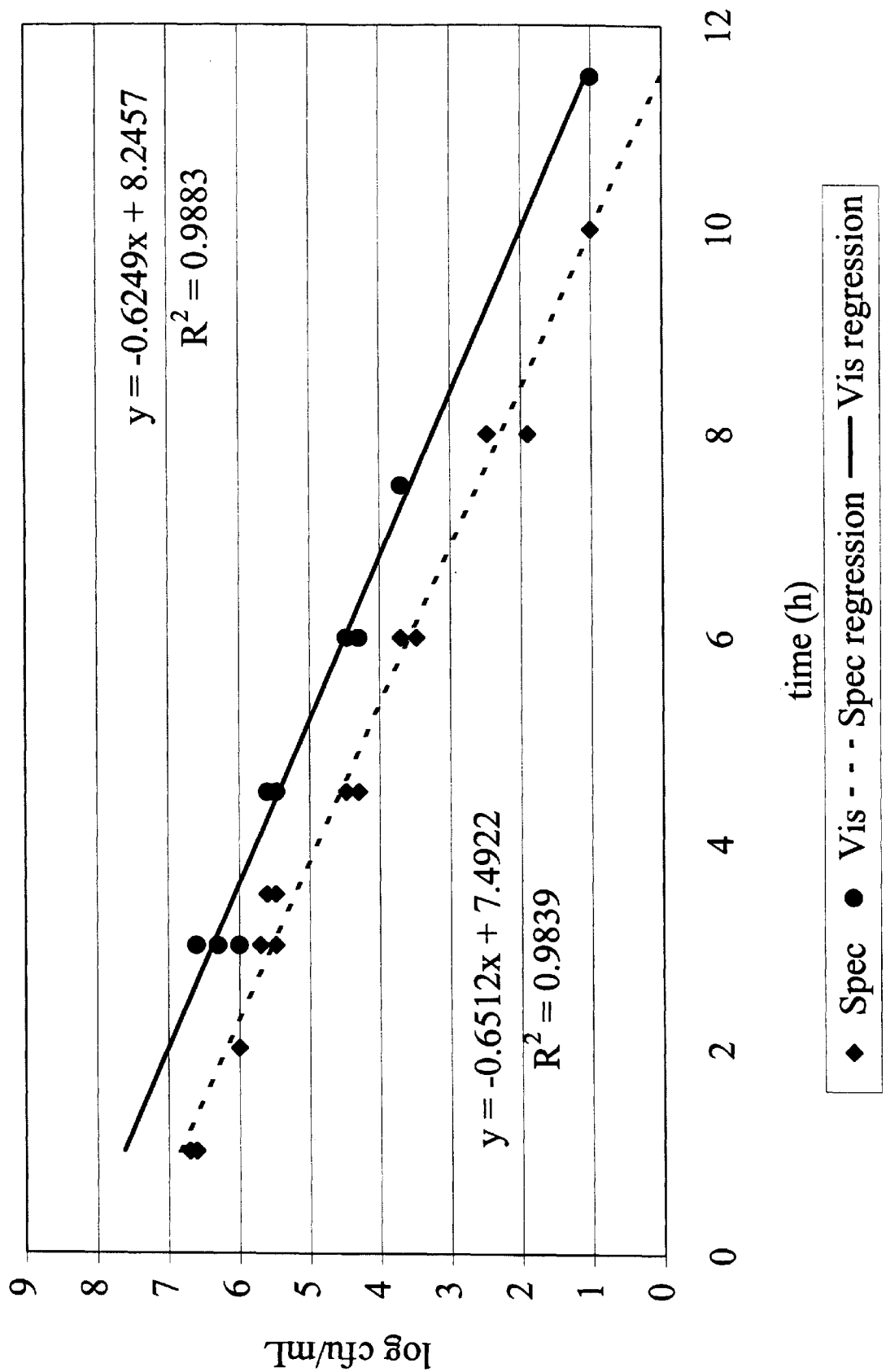
FIG 5: *E. coli* Correlation Curves

BIOLOGICAL ASSAY FOR MICROBIAL CONTAMINATION

BACKGROUND OF THE INVENTION

1. Field of the Invention

This invention generally relates to methods for rapid and inexpensive determination of the level or concentration of total coliforms or *E. coli* in a liquid sample. The invention provides a simple assay using a reagent mixture containing an indicator compound which changes color upon cleavage by the beta galactosidase enzyme specifically found in coliforms or the beta glucuronidase enzyme unique to *E. coli*. These assays are particularly useful in detecting total coliform or *E. coli* contamination in recreational water, drinking water, food processing operations and other matrices which may be contaminated with coliforms and *E. coli*.

2. Description of the Prior Art

Pathogenic microorganisms, including coliforms, can be present in high concentrations in the feces of infected humans and animals. Contamination of water with sewage or fecal wastes may be a serious threat to human health. Contamination of meat and poultry by exposure to fecal material during processing also poses a threat to human health. The sanitary quality of drinking water, recreational water, wash water or areas in which butchering and processing take place must be carefully monitored.

Numerous methods for testing the sanitary quality of water are available but in general they require 24–48 h for growth of the microorganisms. These methods include monitoring for the presence of indicator bacteria, total coliforms and fecal coliforms. The total coliform group includes certain strains of bacteria which are generally not found in fecal material, i.e. Klebsiella, Enterobacter, Citrobacter, Serratia sp., as well as bacteria which may be found in soil and on vegetation but are infrequently isolated from feces. The fecal coliform group is comprised principally of the bacterium *Escherichia coli*, the predominant coliforms found in feces, but does include some Klebsiella and Enterobacter sp. *E. coli* are found in the intestines of humans and animals and are present at a cell density in the range of $10^7$ to $10^8$ cells per gram of feces.

Test methods for the determination of total coliforms include the use of chromogenic and fluorogenic chemicals, i.e. orthonitrophenyl galactoside (ONPG), chlorophenylred galactoside (CPRG), methylumbelliferone-galactoside, often coupled with membrane filtration technology. Test methods for detecting fecal coliforms also include but are not limited to the use of fluorogenic and chromogenic chemicals, i.e. methylumbelliferyl glucuronide (MUG), resorufin D glucuronide, and fluorescein diglucuronide. Techniques currently used require 24 to 48 hours to assess contamination levels and often require additional testing to confirm the presence of coliforms and/or *E. coli*.

Many commercially available assays for the detection of coliforms or *E. coli* use membrane filter methods from Standard Methods for Examination of Water and Waste Water (Standard Methods for Examination of Water and Waste Water, 18th ed., Greenberg et al. eds, pp. 9-45 to 9-64 [1992]) in which a specific volume of water sample or dilution(s) of the water sample are passed through a sterile 0.45 μm membrane filter. The filter is then removed from the filter apparatus and placed on top of a solid agar substrate for growth at a specified temperature for a specified time period. These assays require days for growth, enumeration and confirmation of the contaminant of interest. Other commercial assays use a reagent mixture to which the sample is added, or the sample to which the reagent is added (Colilert®, Edberg U.S. Pat. Nos. 4,925,789 and 5,429,933; Colisure™, Millipore; Coliquik™, Hach), followed by incubation for 18–28 h to obtain presence/absence results with respect to coliform and *E. coli* contamination. Most Probable Number (MPN) analysis using the same or similar reagent mixtures can also be performed to yield the most probable number of coliforms and *E. coli* present in the water sample within 24–48 h.

U.S. Pat. No. 5,420,017 to Tuompo describes a method for detecting microorganisms by using a filter to trap microorganisms. A test solution is added which contains a chromogenic reagent which can be reduced by microbial dehydrogenase enzymes to yield a colored product. Detection limits range from $10^5$ to $10^6$ colony forming units (cfu)/ml.

U.S. Pat. No. 4,923,804 to Ley et al. describes a method that is specific for detecting and enumerating *E. coli* in a water sample. The method is carried out using standard membrane filtration analysis with a chromogenic reagent, which if subjected to β-glucuronidase activity as a result of the presence of *E. coli* produces clearly defined coloring on the membrane filter representative of individual colonies grown from *E. coli* cells in the test specimen.

U.S. Pat. Nos. 4,925,789 and 5,429,933 to Edberg describe a method for determining the presence or absence of a predetermined target microbe in a sample by addition of test medium to the sample or of the sample to test medium. The test medium is a defined substrate providing a selective growth medium for the target microbe and includes a specific nutrient which only the target microbe can metabolize. The sample altering moiety attached to the specific nutrient is activated to change the sample only if the specific nutrient is metabolized by the target microbe. The sample-altering moiety can be a material which changes the color of the sample, an electrical characteristic of the sample or some other detectable characteristic of the sample. Sterility of the test matrix is not required. In addition, U.S. Pat. No. 5,429,933 includes the use of an antibiotic to inhibit growth of non-target microbes in the medium specified and an accelerant which hastens the growth of target microbes to the log phase of growth. U.S. Pat. No. 4,925,789 suggests that MPN analysis using the reagent mixture can be performed.

U.S. Pat. No. 5,610,029 to Ehrenfeld et al. describes an optimized medium for determining the presence of target microorganisms within 18–24 h. A "microbe-specific medium" allows substantial growth of only the target microbe and includes media containing one or more antibiotics specific for inhibiting growth of microorganisms other than the target microbe.

Detection of microbial by-products or metabolites as a means for detecting bacterial contamination have also been developed. Some of these techniques include detection of bacterial endotoxins using a Limulus Lysate Assay, detection of bacteria using electrical impedance measurements, ATP assays, and carbon-14 labeled substrate assays. These tests have not been widely accepted because they do not specifically determine the presence and/or concentration of microorganisms associated with human or animal intestinal flora which can be used to predict whether or not putative pathogens are present.

SUMMARY OF THE INVENTION

An object of this invention is to provide a new method for rapidly and accurately detecting and indicating the presence of viable coliforms or *E. coli* in a liquid sample.

It is also an object of this invention to provide a semi-quantitative method for rapidly and accurately quantifying and indicating the concentration of viable coliforms or E. coli in a liquid sample.

It is a further object of this invention to provide a method in which the detection is by use of spectrophotometry.

It is a further object of this invention to provide a method in which the detection is accomplished using a spectrophotometer for determination of absorbance changes at 405 nm for coliforms and at 355 nm for E. coli.

It is a further object of this invention to provide a method in which the detection is clearly visible to the human eye. The use of long wave UV is required for the fecal coliform test.

It is a further object of this invention to provide a rapid and accurate method for quantitatively detecting and indicating viable coliforms or E. coli in a liquid sample by correlating the time required for detection to the number of viable coliforms or E. coli in the sample.

It is another object of this invention to provide a kit for rapidly and accurately determining and indicating the presence or absence of coliforms or E. coli in a liquid sample. Uses of the kit may be for detecting the above coliforms or E. coli, however other uses are possible. Each component of the kit(s) may be individually packaged in its own suitable container. The individual containers may also be labeled in a manner which identifies the contents. Moreover, the individually packaged components may be placed in a larger container capable of holding all desired components. Associated with the kit may be instructions which explain how to use the kit. These instructions may be written on or attached to the kit.

The method for determining the concentration of viable coliforms or E. coli in a liquid according to the invention, comprises the steps of:

obtaining a sample to be tested from a source where contamination is suspected;

mixing said sample with an indicator reagent in a container to form a liquid test sample, wherein said indicator reagent includes an indicator compound that undergoes a change detectable by spectrophotometric or visual methods upon cleavage by a beta galactosidase enzyme found in coliforms or a beta glucuronidase enzyme unique to E. coli;

detecting spectrophotometrically or visually a predetermined detectable change in said liquid test sample due to coliforms or E. coli being in contact with said indicator reagent;

measuring an elapsed time for said predetermined detectable change to occur in said liquid sample, said elapsed time indicating the concentration of viable coliforms or E. coli in said liquid at the time of selection of said sample.

Alternatively, the method for detecting the presence/absence of viable coliforms or E. coli in a sample according to the invention, comprises the steps of:

obtaining a sample to be tested from a source where contamination is suspected;

mixing said sample with an indicator reagent in a container to form a liquid test sample, wherein said indicator reagent includes an indicator compound that undergoes a change detectable by spectrophotometric or visual methods upon cleavage by a beta galactosidase enzyme found in coliforms or a beta glucuronidase enzyme unique to E. coli;

incubating said liquid test sample and control sample at about 35° C. for about 24 h or less; and detecting a predetermined detectable change to detect one colony forming coliform or E. coli in the total sample volume tested.

The kit of the invention for detecting a concentration of viable coliforms or E. coli in a sample, comprises:

a container for holding the sample to be tested;

an indicator reagent in said container or in a separate container in which said sample is added and a liquid test sample is formed, wherein said indicator reagent undergoes a predetermined detectable change upon cleavage of the indicator compound as a result of contact with a viable coliform or E. coli, said indicator reagent being positionable within said container; and instructions for carrying out the detection method as discussed above.

According to the invention, methods and kits are provided for detecting the presence of and quantifying the concentration of viable coliforms or E. coli in a liquid sample. An indicator reagent which undergoes a visible color change when it is cleaved by enzymes unique to the coliform group of bacteria is used in the coliform test and a reagent which becomes fluorescent when it is cleaved by enzymes unique to E. coli is used in the E. coli test. Only viable microorganisms can cleave the reagent. Dead microorganisms have no effect.

BRIEF DESCRIPTION OF THE DRAWINGS

The foregoing and other objects, aspects and advantages will be better understood from the following detailed description of the preferred embodiments of the invention with reference to the drawings, in which:

FIG. 4 is a graph of the correlation between time and concentration of coliforms using spectrophotometric and visual endpoint determinations; and FIG. 5 is a graph of the correlation between time and concentration of E. coli using spectrophotometric and visual endpoint determinations.

DETAILED DESCRIPTION OF THE PREFERRED EMBODIMENTS OF THE INVENTION

Figure 1:
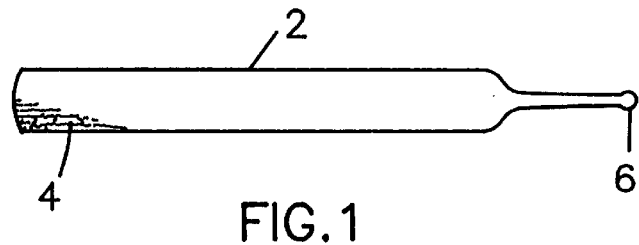
FIG. 1 is a side view of an ampoule containing dry medium components under vacuum, a part of the kit for use in quantifying the number of coliforms or E. coli present in a liquid sample.

A new technique for rapidly and accurately detecting coliform and E. coli contamination in a liquid has been discovered. This technique is useful for any application in which it is necessary to monitor the biological contamination level, for example drinking water, recreational waters, food processing waters and medical laboratories. The water sample is added to a reagent mixture containing a chromogenic agent which yields a yellow chromophore upon cleavage by the beta galactosidase enzyme unique to the coliform group of bacteria or a reagent mixture containing a fluorogenic agent which yields a bright blue fluorophore upon cleavage by the beta glucuronidase enzyme unique to E. coli.

The nutrient formulation includes a buffer, such as phosphate buffer, capable of maintaining the pH of the sample at or near pH 7, tryptic soy broth (TSB) without glucose, succinate, and isopropylthiogalactopyranoside (IPTG) which is an inducer of beta galactosidase enzyme in coliforms. TSB is a nondefined mixture component which provides vitamins, minerals and trace elements, but no significant carbon source other than amino acids. TSB without glucose can be used by many microbes as well as the target microorganisms of the present invention for growth. Antibiotics are optionally excluded from the nutrient formulation.

Succinate is a carbohydrate source for growing organisms and is used to increase biomass. It does not inhibit production or activity of the beta galactosidase enzyme in the coliform assay but does inhibit production/activity of the glucuronidase enzyme of *E. coli*. Therefore, succinate is not included in the reagent powder mixture for the *E. coli* assay.

Succinate is used in an amount effective to enhance biomass formation in the coliform assay and is usually 0.05–0.2/ml, preferably 0.1–0.15 mg/ml of sample at which concentration the biomass is rapidly increased. The addition of increased amounts of sodium succinate, for example, 0.2 mg/ml of sample, results in increased biomass of non-target microbes able to use succinate as a carbon source.

The concentration of TSB without glucose in the test ampoule after adding the sample directly without dilution should be sufficient to provide the nutrients to sustain the viability and reproduction of the target microbes, and is usually 5–15 mg/ml of sample, preferably 8–12 mg/ml, more preferably 9–11 mg/ml and most preferably 10 mg of TSB/ml of sample after direct addition of the sample to the test ampoule.

The total amount of the TSB without glucose, buffer, IPTG and succinate is sufficient to sustain the viability of the target microbe (coliform) and to result in replication of the target microbe to generate sufficient biomass to produce a detectable change in the sample due to beta-galactosidase activity and is usually in the range of 10–25 mg/ml, preferably 10–20 mg/ml, more preferably 13–18 mg/ml, and most preferably 16.8–17.3 mg/ml. For example, a mixture of TSB/buffer and succinate in a ratio of 10 mg:7 mg:0.1 mg respectively is delivered in a weight of 136.8 mg for a sample of 8 ml or 171 mg for a sample of 10 ml or 342 mg for a sample of 20 ml. IPTG is used in an amount to induce the production of beta-galactosidase, and is usually in the range of 0.01–0.05 mg/ml, preferably 0.015–0.05 mg/ml, and most preferably 0.02 mg/ml of sample.

ONPG is used in an amount sufficient to produce a spectrophotometrically or visually detectable change in response to being cleaved by beta-galactosidase enzymes, and is usually in the range of 0.5–5 mg/ml, preferably 1–3 mg/ml, and most preferably 1.25 mg/ml of sample.

MUG is used in an amount sufficient to produce a spectrophotometrically or visually detectable change in response to being cleaved by beta-glucuronidase enzyme, and is usually in the range of 0.005–0.5 mg/ml, preferably about 0.05 mg/ml of sample.

The buffer may be any buffer which is used in a sufficient quantity to maintain the pH of the sample to be tested at about 7. Preferably, the buffer is a mixture of $NaH_2PO_4$ and $Na_2HPO_4$, and is usually in the range of 5–9 mg/ml, preferably 6.5–7.6 mg/ml, and most preferably 7 mg/ml of sample.

The sample is mixed and incubated at a temperature which allows rapid growth of the microorganism(s) being assayed and is usually 32–37° C., preferably at or near 35° C. The absorbance spectrum of each coliform test sample is monitored at or near the lambda max of the chromophore generated (at 405 nm, the lambda max of the nitrophenol chromophore generated by cleavage of the indicator reagent, ONPG, by the beta galactosidase enzyme in the coliform test, and at 355 nm, the lambda max of the fluorophore produced by cleavage of the indicator reagent, MUG, by the beta glucuronidase enzyme, in an *E. coli* test).

Spectrophotometric monitoring of the reaction mixture results in detection of a positive endpoint (i.e. increase in Absorbance of about 0.05 absorbance units) earlier than is possible for visual detection of the bright yellow color or detection of the bright blue fluorescence under long wave UV. Detection by visual or spectrophotometric methods can easily be accomplished within about 24 hours or less. The concentration of coliforms in the sample can be determined over a large concentration range, with spectrophotometric detection of 20 coliforms/ml within about 10 h, and visual detection within about 11.5 h. The concentration of *E. coli* in the sample can be determined over a large concentration range, with the detection of 10 *E. coli*/ml within about 12 h, preferably within 10 h using the spectrophotometric assay, and within 12 h for visual detection under long wave UV. Applicant has established a correlation between time to positive reaction (visual color change or spectrophotometric endpoint) and concentration of target microorganism (coliforms or *E. coli*) in the original sample.

EXAMPLES

Figure 2:
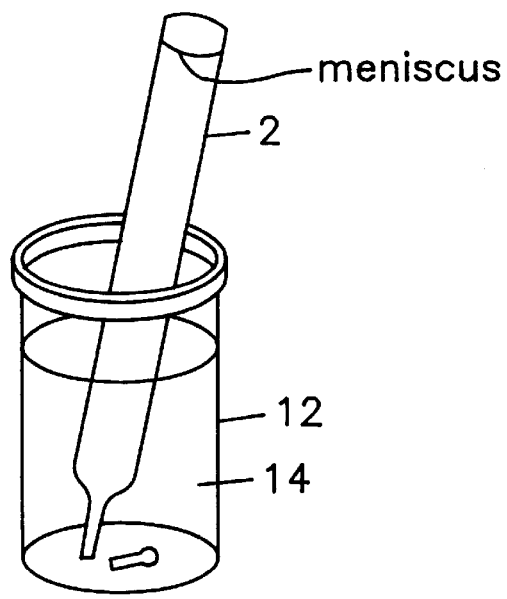
FIG. 2 is a view of the ampoule from FIG. 1 in the snapping cup containing the water sample to be tested. The tip of the ampoule is broken off in the snapping cup and the ampoule is filled by the action of the vacuum in the tube.
Figure 3:
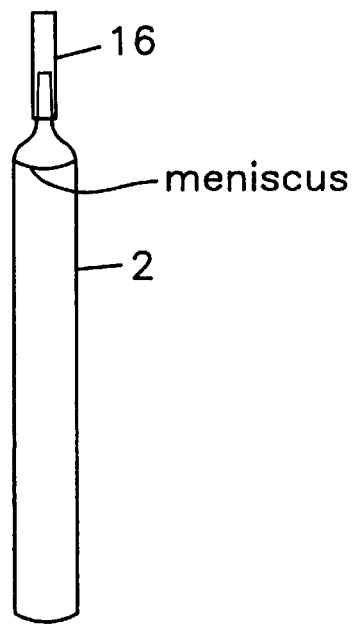
FIG. 3 is a side view of the ampoule of FIG. 2 filled with the sample to be tested and with the safety sleeve in place over the broken tip.

A representative example of a vessel which can be used in the practice of this invention is shown in FIG. 1–FIG. 3. As shown in FIG. 1, a sealed indicator vial or ampoule 2 under vacuum contains a substantially anhydrous mixture of indicator reagent 4. The ampoule terminates in a sealed tip 6.

As shown in FIG. 2, the tip 6 is placed in a snapping cup 12 which contains the sample to be tested 14, wherein the tip 6 is broken by pressing against the inside of the cup, and the test sample 14 is sucked by the vacuum into the ampoule 2, whereupon the sample to be tested is mixed with the indicator reagent 4.

As shown in FIG. 3, the filled ampoule 2 is then removed from the cup and a safety sleeve 16 is placed over the broken tip to prevent spillage or contamination of the contents.

Additional details concerning the kit can be found in U.S. Pat. No. 5,159,799, which is hereby incorporated by reference in its entirety.

EXAMPLE 1

Semi-quantitative determination of the presence of coliforms

In one tube, which is the test, approximately 1.25 mg of indicator (25 µl of stock solution at 50 mg/ml) per ml of sample, preferably ONPG, is added to the water and nutrient mixture per ml of sample. The indicator solution includes ONPG at a concentration of 50 mg/ml in sterile distilled water/acetone solution. Addition of 125 µl of the ONPG indicator stock solution into 5 ml of sample results in the delivery of 1.25 mg/ml (total of 6.25 mg in 5 ml) into each tube which contains a water sample to be tested.

The second tube is the control tube containing the water sample mixed with the nutrient mixture, no indicator, ONPG, to allow for comparison of the test sample with this control to accommodate sample color and/or reaction with nutrient mixture.

A third tube is the spectrophotometric blank which contains the indicator reagent in sterile water.

Other chromogenic indicators, i.e. CPRG, methylumbelliferyl galactoside, resorufin based reagents, trifluoromethylumbelliferyl galactoside, and fluorescein based reagents may be used although time to obtain positive results will vary from those obtained using ONPG.

At this point, the tubes should be incubated at 32–37° C., preferably at or near 35° C. in a heat block or incubator. It has been found that this can be accomplished by placing the tubes in the pocket of the individual performing the test or by placing the ampoules in a heat block or incubator. Samples are spectrophotometrically and visually compared at predetermined intervals, preferably every hour, until a change in absorbance at 405 nm of about 0.05 absorbance units and/or visual yellow color, as compared to the control sample, is observed. It has been found that the time required for the replication of coliforms in the sample to reach a critical mass sufficient to release nitrophenol into the medium resulting in a change in the absorbance at 405 nm and subsequently to yield a visible yellow color can be correlated to the coliform concentration in the water sampled and tested. Table 1 below shows the time for determining the concentration of coliforms in the original sample.

TABLE 1

SEMI-QUANTITATIVE DETERMINATION OF COLIFORM USING ONPG

|  | Time (h) | Initial Concentration (per ml) |
|---|---|---|
| Spectrophotometric | 2 | $2.5 \times 10^6$ |
| Spectrophotometric | 10 | $2 \times 10^1$ |
| Visual | 3 | $3.5 \times 10^6$ |
| Visual | 11 | $10^1$ |

A representative plot of correlation between time and initial concentration of viable coliforms is shown in FIG. 4 and Tables 2 and 3.

TABLE 2

Coliform Spectrophotometric Calibration

| time (h) | cfu/ml |
|---|---|
| 2 | $2.5 \times 10^6$ |
| 3 | $4.2 \times 10^5$ |
| 4 | $7 \times 10^4$ |
| 5 | $1.2 \times 10^4$ |
| 6 | $1.9 \times 10^3$ |
| 7 | $3.2 \times 10^2$ |
| 8 | $5.4 \times 10^1$ |
| 9 | $9 \times 10^0$ |
| 10 | $2 \times 10^0$ |

TABLE 3

Coliform Visual Calibration

| time (h) | cfu/ml |
|---|---|
| 2 | $1.8 \times 10^7$ |
| 3 | $3.5 \times 10^6$ |
| 4 | $6.8 \times 10^5$ |
| 5 | $1.3 \times 10^5$ |
| 6 | $2.6 \times 10^4$ |
| 7 | $5 \times 10^3$ |

TABLE 3-continued

Coliform Visual Calibration

| time (h) | cfu/ml |
|---|---|
| 8 | $9.7 \times 10^2$ |
| 9 | $1.9 \times 10^2$ |
| 10 | $3.6 \times 10^1$ |

EXAMPLE 2

Semi-quantitative determination for the presence of E. coli

The nutrient formulation in Example 1 was used, except that succinate is absent because succinate inhibits the production/activity of the glucuronidase enzyme of E. coli, which would result in increased time to positive reaction. The indicator molecule is MUG, used at 0.05–1 mg/ml of sample, which is cleaved by the glucuronidase enzyme to produce a fluorophore visible under long wave UV. Spectrophotometric monitoring at 355 nm detects the release of the fluorophore after enzymatic cleavage of MUG. An increase of about 0.05 absorbance units constitutes a positive reaction. Detection of a bright blue color in the test sample when compared to the control sample is a positive visual reaction. Furthermore, in the E. coli semi-quantitative assay, an incubation temperature of 44.5° C. does not result in more rapid E. coli detection. Growth occurs, but enzyme production/activity as measured by fluorophore generation appears to be inhibited.

Table 4 below shows the time for determining the concentration of E. coli in the sample.

TABLE 4

SEMI-QUANTITATIVE DETERMINATION OF E. coli USING MUG

|  | Time (h) | Initial Concentration (per ml) |
|---|---|---|
| Spectrophotometric | 1 | $10^7$ |
| Spectrophotometric | 9 | $4 \times 10^1$ |
| Visual | 2 | $10^7$ |
| Visual | 10.5 | $\geq 10^1$ |

A representative plot of correlation between time and initial concentration of viable E. coli is shown in FIG. 5 and Tables 5 and 6.

TABLE 5

E. coli Spectrophotometric Calibration

| time (h) | cfu/ml |
|---|---|
| 2 | $1.5 \times 10^6$ |
| 3 | $3.5 \times 10^5$ |
| 4 | $7.7 \times 10^4$ |
| 5 | $1.7 \times 10^4$ |
| 6 | $3.8 \times 10^3$ |
| 7 | $8.6 \times 10^2$ |
| 8 | $1.9 \times 10^2$ |
| 9 | $4.3 \times 10^1$ |
| 10 | $1.0 \times 10^1$ |

TABLE 6

E. coli Visual Calibration

| time (h) | cfu/ml |
| --- | --- |
| 2 | $9.9 \times 10^6$ |
| 3 | $2.3 \times 10^6$ |
| 4 | $5.6 \times 10^5$ |
| 5 | $1.3 \times 10^5$ |
| 6 | $3.1 \times 10^4$ |
| 7 | $7.4 \times 10^3$ |
| 8 | $1.8 \times 10^3$ |
| 9 | $4.2 \times 10^2$ |
| 10 | $1 \times 10^2$ |

EXAMPLE 3

Presence-Absence test for coliforms and E. coli

Overnight incubation, for example, about 24 h at 32–37° C. under the condition in Example 1 for coliforms and Example 2 for E. coli, detected 1 cfu coliform in the total sample volume or 1 cfu E. coli in the total sample volume.

EXAMPLE 4

Analysis of a Natural Water Sample

Table 7 below shows results of Natural Water Sample Testing.

Sample A is raw water obtained from a freely running creek in Potomac, Md. Sample B is Sample A spiked with microorganisms other than coliforms. Sample C is Sample A spiked with E. coli. Initial concentration levels were confirmed using serial dilutions and plating on EMB/MAC agar for determination of total coliforms and E. coli. Sample D is a second sample of Creek Water obtained from the same creek a week later.

TABLE 7

ANALYSIS OF NATURAL WATER SAMPLE

| | Time (h) | Initial Concentration (cfu/mL) |
| --- | --- | --- |
| A. Spectrophotometric (coliforms) | 4.5 | $10^4$ |
| Spectrophotometric/visual (E. coli) | >10 | Present (24 h) |
| B. Spectrophotometric (coliforms) | 4.5 | $10^4$ |
| Spectrophotometric/visual (E. coli) | >10 | Present (24 h) |
| C. Spectrophotometric (coliforms) | 2 | $2 \times 10^6$ |
| Spectrophotometric/visual (E. coli) | 7 | $10^2$ |
| D. Spectrophotometric (coliforms) | 7 | $3 \times 10^{2}*$ |
| Spectrophotometric/visual (E. coli) | >10 | Present (24 h) |

*visual positive at 9 h for Sample D, coliforms.

While the invention has been described in terms of its preferred embodiments, those skilled in the art will recognize that the invention can be practiced with modification within the spirit and scope of the appended claims.

What is claimed is:

1. A method for determining the concentration of viable coliforms or E. coli in a liquid, comprising the steps of:
    obtaining a sample of said liquid to be tested from a source where contamination is suspected;
    mixing said sample with an indicator reagent in a container to form a liquid test sample, wherein said indicator reagent includes an indicator compound that undergoes a change detectable by spectrophotometric or visual methods upon cleavage by a beta galactosidase enzyme found in coliform or a beta glucuronidase enzyme unique to E. coli;
    detecting spectrophotometrically or visually said detectable change in said indicator compound in said liquid test sample due to viable coliform or E. coli being in contact with said indicator reagent;
    measuring an elapsed time for said detectable change in said indicator compound to occur in said liquid test sample, said elapsed time indicating the concentration of viable coliform or E. coli in said liquid at the time of selection of said sample, whereby only one liquid test sample is used to determine said concentration in said liquid.

2. The method of claim 1, wherein said liquid sample to be tested is water.

3. The method of claim 1, wherein said indicator reagent comprises:
    i) buffer that maintains a pH of about 7,
    ii) tryptic soy broth without glucose,
    iii) succinate,
    iv) isopropylthiogalactopyranoside; and
    v) an indicator compound that undergoes a color change upon cleavage by beta galactosidase.

4. The method of claim 1, wherein the indicator reagent comprises:
    i) buffer that maintains a pH of about 7,
    ii) tryptic soy broth without glucose, and
    iii) an indicator compound that undergoes a detectable change upon cleavage by beta glucuronidase, and wherein said indicator reagent does not contain succinate.

5. The method of claim 1, wherein said indicator compound is orthonitrophenyl galactoside for detecting coliforms.

6. The method of claim 1, wherein said indicator compound is methylumbelliferyl glucuronide for detecting E. coli.

7. The method of claim 5, wherein the concentration of orthonitrophenyl galactoside in the sample is about 0.5 to about 5 mg/ml of sample.

8. The method of claim 6, wherein the concentration of methylumbelliferyl glucuronide in the sample is about 0.05 to about 0.5 mg/ml of sample.

9. The method of claim 7 or 8, wherein said detecting step is performed spectrophotometrically at predetermined intervals until a change in absorbance of about 0.05 absorbance units has occurred.

10. The method of claim 7 or 8, wherein said detecting step is performed visually at predetermined intervals until a bright yellow color as compared to the control is observed for the coliform test or a fluorescent blue color is observed under long wave UV for the E. coli test.

11. The method of claim 1, wherein said step of measuring an elapsed time for said detectable change in said indicator compound includes the step of:
    periodically comparing said liquid sample in said container from the time said indicator reagent is mixed with the liquid sample with a control liquid sample contained in a second container, wherein said control liquid sample is devoid of said indicator reagent, until said detectable change is observed in said liquid sample including said indicator reagent by comparison to said control sample devoid of said indicator reagent wherein a third container containing sterile water with said indicator reagent is used as a blank for the spectrophotometric determinations.

12. The method of claim 11, further comprising a step of incubating said container containing said liquid sample and said second container containing said control liquid sample.

13. The method of claim 1, wherein said elapsed time to detect about 20 viable coliforms/ml spectrophotometrically is within about 10 h, and visually is within about 11.5 h.

14. The method of claim 1, wherein said elapsed time to detect about 10 viable *E. coli*/ml spectrophotometrically is within about 10 h, and visually is within about 12 h.

15. A method of claim 1, wherein said concentration of viable coliforms or *E. coli* in said liquid is cfu/ml.

16. A method of claim 1, with the proviso that the method is not most probable number analysis.

17. A method of claim 1, further comprising determining at predetermined intervals whether said detectable change in said indicator compound has occurred.

18. A method of claim 17, wherein the predetermined intervals are hourly.

19. A kit for detecting the concentration of viable coliforms in a liquid sample, comprising:

a first container for holding said liquid sample; and a second container comprising an indicator reagent under vacuum, whereby said second container is insertable into said first container, whereby releasing said vacuum in said second container when said second container is positioned within said first container, results in the filling of said second container with said liquid sample present in said first container, and wherein said indicator reagent undergoes a visible or spectrophotometrically detectable change upon cleavage as a result of contact with a viable coliform producing a beta-galactosidase enzyme.

20. A kit of claim 19, wherein said indicator reagent is orthonitrophenyl galactoside.

21. A kit of claim 19, wherein said indicator reagent is positionable within said second container.

22. The kit according to claim 19, wherein said indicator reagent is methylumbelliferyl glucuronide for detecting *E. coli*.

23. A kit for detecting the concentration of viable *E. coli* in a liquid sample, comprising:

a first container for holding said liquid sample; and a second container comprising an indicator reagent under vacuum, whereby said second container is insertable into said first container, whereby releasing said vacuum in said second container when said second container is positioned within said first container, results in the filling of said second container with said liquid sample present in said first container, and wherein said indicator reagent undergoes a visible or spectrophotometrically detectable change upon cleavage as a result of contact with a viable coliform producing a beta-galactosidase enzyme.

24. A kit of claim 23, wherein said indicator regent is orthonitrophenyl galactoside.

25. A kit of claim 23, wherein said indicator reagent is positionable within said second container.

\* \* \* \* \*